United States Patent [19]
Cook et al.

[11] Patent Number: 6,078,036
[45] Date of Patent: Jun. 20, 2000

[54] LASER SOFT DOCKING SYSTEM FOR MEDICAL TREATMENT SYSTEM

[75] Inventors: Thomas A. Cook, San Rafael, Calif.; George Spalek, Santa Fe, N. Mex.

[73] Assignee: Intraop Medical, Inc., Sunnyvale, Calif.

[21] Appl. No.: 09/073,561

[22] Filed: May 6, 1998

[51] Int. Cl.[7] .............................. A61B 6/08; H01J 37/30
[52] U.S. Cl. ................................... 250/206.1; 250/208.2; 356/400; 378/206
[58] Field of Search .............................. 250/206.1, 206.2, 250/208.2, 231.13, 234, 235, 492.3; 356/138, 153, 154, 399, 400, 401; 378/205, 206, 65; 606/130

[56] References Cited

U.S. PATENT DOCUMENTS

| | | | |
|---|---|---|---|
| 4,815,845 | 3/1989 | Colbaugh et al. | 356/153 |
| 5,095,386 | 3/1992 | Scheibengraber | 359/668 |
| 5,321,271 | 6/1994 | Schonberg et al. | 250/492.3 |
| 5,553,112 | 9/1996 | Hardy et al. | 378/206 |

OTHER PUBLICATIONS

An 8 page document headed Intraop Mobetron, A Mobile Electron Beam Intraoperative Treatment System dated Jan. 1998.

*Primary Examiner*—John R Lee
*Attorney, Agent, or Firm*—Stanley Z. Cole; William McClellan

[57] ABSTRACT

A soft docking system is provided for a medical treatment system, such as an intraoperative electron beam therapy system. The medical treatment system includes a treatment head, an applicator having a fixed position relative to a patient and apparatus for adjusting the position of the treatment head relative to the applicator. The soft docking system includes one or more sensing assemblies for sensing a position of the treatment head relative to the applicator and providing one or more position signals representative thereof, and a display responsive to the position signals for indicating the position of the treatment head relative to the applicator. The position of the treatment head may be adjusted so that the display indicates a desired postion. The docking system may provide an interlock signal to prevent application of the electron beam until the treatment head and the applicator are correctly aligned.

20 Claims, 4 Drawing Sheets

LASER SOFT DOCKING SYSTEM FOR MEDICAL TREATMENT SYSTEM

FIELD OF THE INVENTION

This invention relates to systems and methods for positioning a medical treatment system relative to an applicator and, more particularly, to a laser soft docking system for positioning an intraoperative electron beam therapy system relative to an applicator.

BACKGROUND OF THE INVENTION

Radiation has long been used intraoperatively to treat a variety of cancers by delivering a high local dose of radiation directly to a tumor through the operative site. Early intraoperative radiation treatment methods utilized X-rays as the radiation source. More recent intraoperative therapy installations have employed beams of high energy electrons as the radiation source to provide a homogeneous dose of radiation with a rapid falloff in radiation intensity beyond the treatment volume, thereby minimizing exposure of noncancerous tissue to the radiation.

In a typical intraoperative electron beam therapy procedure, the surgeon removes the bulk of patient's tumor so that minimal residual disease remains. The attending radiation oncologist selects the electron beam energy and field size required to treat the target volume. A single radiation dose is then delivered to the tumor site, while the dose delivered to normal tissues is kept to a minimum. An example of an intraoperative electron beam therapy system is disclosed in U.S. Pat. No. 5,321,271 issued Jun. 14, 1994 to Schonberg et al.

During intraoperative treatment of cancer using electron beams, special tubes called applicators are used to shape and guide the electron beam to the treatment site inside the patient without allowing the beam to expose healthy tissue. The treatment head which produces the electron beam must be accurately aligned to the applicator to preserve beam symmetry and uniformity.

In one alignment approach known as hard docking, the applicator is attached directly to the treatment head. Hard docking is not favored because the applicator is simultaneously in contact with the patient and the relatively large and heavy treatment head of the treatment system. If the treatment head is accidentally moved, the applicator may injure the patient.

In soft docking techniques, the treatment head does not physically contact the applicator. One prior art soft docking approach uses laser fan beam alignment to a metal rod that is aligned to the axis of the applicator. The base of the rod and the top of the applicator are located on the machine's isocenter. The disk and rod docking scheme requires that the top of the applicator be at the machine's isocenter height and that the centerline of the applicator be in a plane perpendicular to the center of rotation of the treatment machine. Portable radiotherapy machines have no fixed isocenter position, and the patient plane is strictly determined by geometry, making the use of this scheme difficult.

In another prior art soft docking approach, multiple laser dots are aligned to a scribed line at the top of the applicator. The multiple laser dot docking scheme requires that eight dots from four pairs of lasers be made to coalesce into four dots on a circle scribed on the top surface of the applicator. Mutually orthogonal alignment motions produce similar behavior of the dots on the applicator surface. This makes it difficult to judge which motion of the treatment head will achieve alignment.

All of the prior art docking techniques have had one or more disadvantages, including risk of injury to the patient, difficulty in achieving alignment and lack of an interlock which prevents operation of the system until alignment is achieved. Accordingly, there is a need for improved methods and apparatus for docking a medical treatment system to an applicator.

SUMMARY OF THE INVENTION

According to a first aspect of the invention, a soft docking system is provided for a medical treatment system that includes a treatment head, an applicator having a fixed position relative to a patient and means for adjusting the position of the treatment head relative to the applicator. The soft docking system comprises one or more sensing assemblies for sensing a position of the treatment head relative to the applicator and providing one or more position signals representative thereof, and a display responsive to the position signals for indicating the position of the treatment head relative to the applicator. The position of the treatment head may be adjusted so that the display indicates a desired position.

The sensing assembly may include sensing assemblies for sensing X position, Y position, Z position, X axis tilt and Y axis tilt of the treatment head relative to the applicator. The sensing assemblies may include a first sensing assembly for sensing X position and Y axis tilt, a second sensing assembly for sensing Y position and X axis tilt and a third sensing assembly for sensing Z position.

The first and second sensing assemblies may each comprise a laser line generator coupled to the treatment head for directing a line beam at a reflective surface rigidly coupled to the applicator so that a portion of the line beam is reflected by the reflective surface. A position photosensor array coupled to the treatment head intercepts the portion of the line beam that is reflected by the reflective surface and provides a position signal. The portion of the line beam reflected by the reflective surface varies with the position of the applicator and is indicative of the position of the applicator. A tilt photosensor array coupled to the treatment head and oriented perpendicular to the line beam senses the tilt of the reflective surface relative to the treatment head and provides a tilt signal.

The third sensing assembly may comprise a laser line generator coupled to the treatment head for directing the line beam at the reflective surface and a Z direction photosensor array coupled to the treatment head and oriented perpendicular to the line beam for sensing the line beam and providing a Z position signal.

The display may comprise first, second, third, fourth and fifth LED arrays representative of X position, Y position, Z position, X axis tilt and Y axis tilt, respectively. An illuminated LED in each of the first, second and third LED arrays is representative of the position of the position head relative to the applicator. An illuminated LED in each of the fourth and fifth LED arrays is representative of tilt angle of the treatment head relative to the applicator.

The docking system may further comprise means responsive to the position signals for generating an interlock signal that inhibits the treatment head from applying a treatment beam to the patient, except when the position signals indicate a desired position of the treatment head relative to the applicator.

According to another aspect of the invention, a method for soft docking of a treatment head to an applicator is provided. The method comprises the steps of sensing a position of the treatment head relative to the applicator and providing one or more position signals representative thereof, indicating the position of the treatment head relative to the applicator on a display in response to the position signals and adjusting the position of the treatment head relative to the applicator so that the display indicates a desired position.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
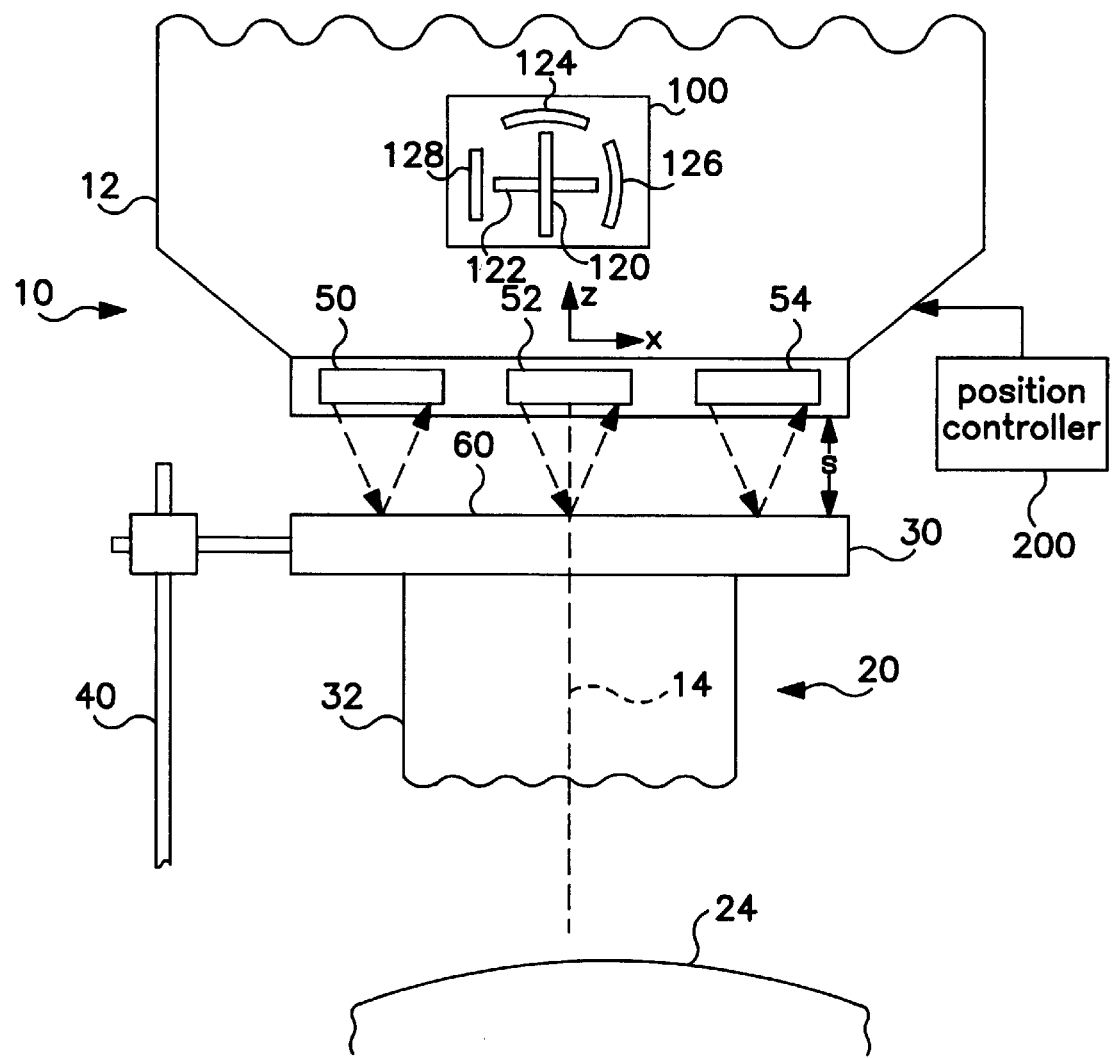
FIG. 1 is a simplified schematic diagram of an example of a medical treatment system incorporating a soft docking system in accordance with the invention.
Figure 2:
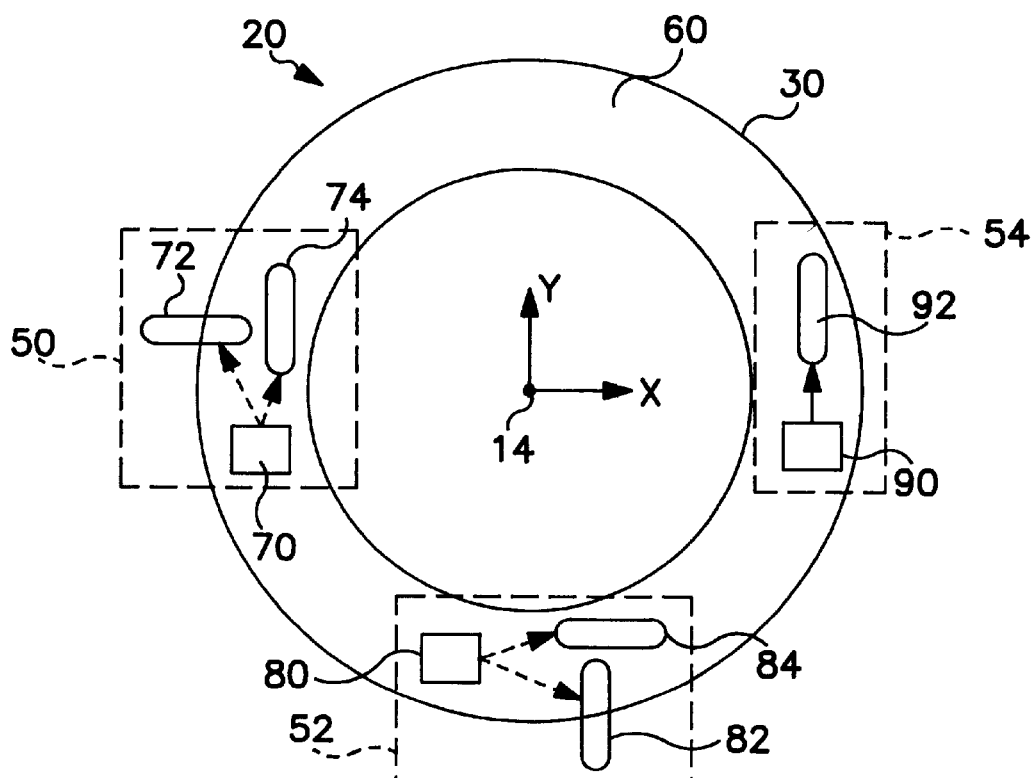
FIG. 2 is a partial schematic diagram of the soft docking system as viewed along the beam axis.

Simplified schematic diagrams of an example of a medical treatment system incorporating a soft docking system in accordance with the invention are shown in FIGS. 1 and 2. A medical treatment system 10 includes a treatment head 12 and an applicator 20. The treatment head 12 applies a treatment beam 14, such as an electron beam, through applicator 20 to a patient 24. The treatment system 10 may, for example, be a Mobetron electron beam therapy system sold by Intraop Medical, Inc. of Santa Clara, California. The applicator 20 includes an annular ring 30 and a cylindrical applicator tube 32 extending from annular ring 30 toward patient 24. The applicator 20 is rigidly supported relative to patient 24 by a support structure 40, which is typically affixed to the surgical table on which the patient 24 is positioned. The treatment head 12 is movable in three dimensions and may be tilted relative to applicator 20.

For proper functioning of the treatment system, the treatment head 12 must be accurately aligned to applicator 20. In particular, the axis of treatment head 12 must be colinear with the axis of applicator tube 32, and a fixed spacing S, typically about 4 centimeters, must be maintained between treatment head 12 and applicator 20. The correct alignment can be ensured by controlling the X, Y and Z position of treatment head 12 relative to applicator 20 and by controlling the tilt angle of treatment head 12 along the X and Y axes relative to applicator 20.

To ensure that the treatment head 12 is properly positioned relative to applicator 20, the treatment system 10 includes a soft docking system. The docking system is "soft" in the sense that the treatment head 12 does not physically contact applicator 14. The soft docking system includes sensing assemblies 50, 52 and 54, which are shown schematically in FIGS. 1 and 2. The sensing assemblies 50, 52 and 54 are mounted in treatment head 12 adjacent to the path of electron beam 14. Each of the sensing assemblies directs a laser beam to a reflective surface 60 of annular ring 30. The laser beams are reflected back to sensing devices within the respective sensing assemblies to determine position and tilt angle, as described in detail below.

As shown in FIG. 2 sensing assembly 50 includes a laser diode 70 and photosensor arrays 72 and 74. Photosensor array 72 determines X position, and photosensor array 74 determines Y axis tilt. Sensing assembly 52 includes a laser diode 80 and photosensor arrays 82 and 84. Photosensor 82 determines Y position, and photosensor array 84 determines X axis tilt. Sensing assembly 54 includes a laser diode 90 and a photosensor array 92, which determines Z position.

The soft docking system further includes a display 100 which may be mounted on treatment head 12 and an electronics unit 110 (FIG. 5) coupled between the sensing assemblies and the display 100. The display 100 preferably includes LED arrays which indicate the position and orientation of the treatment head 12 relative to applicator 20.

Figure 6:
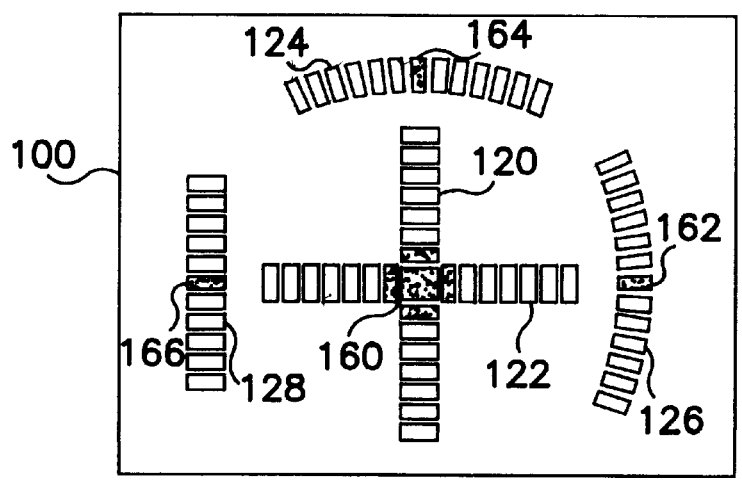
FIG. 6 illustrates the operator display of the soft docking system.

As best shown in FIG. 6, display 100 may include a linear LED array 120 for indicating Y position, a linear LED array 122 for indicating X position, a curved LED array 124 for indicating X axis tilt, a curved LED array 126 for indicating Y axis tilt and a linear array 128 for indicating Z position. In each array an illuminated LED is indicative of position or tilt. As the treatment head 12 position is adjusted, the illuminated LED in one or more of the arrays may change. When proper alignment is achieved, the LED at the center of each array is illuminated. The LED arrays 120 and 122 may form a cross, with an LED 160 at the center of both LED arrays.

Figure 3:
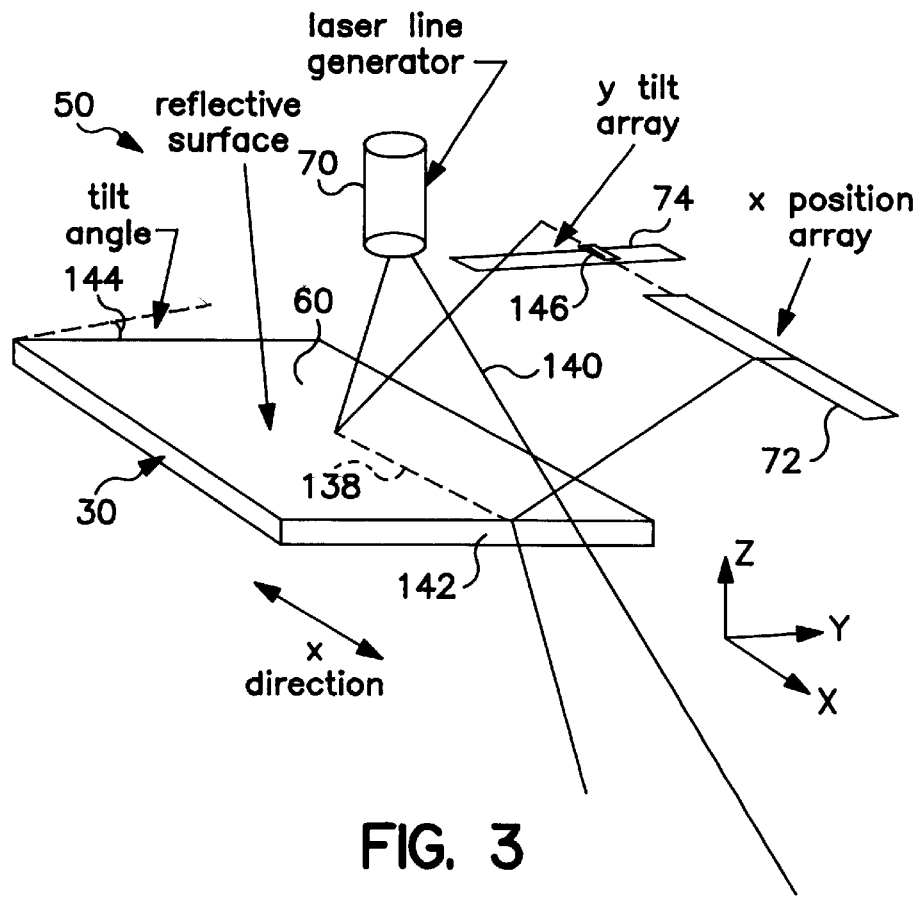
FIG. 3 is a schematic diagram of a first type of laser sensing assembly used in the soft docking system of FIGS. 1 and 2.

A pictorial diagram of an example of sensing assembly 50 is shown in FIG. 3. Laser diode 70 generates a fan line beam 140. Laser diodes which generate a fan line beam are commercially available. The line beam 140 is incident on reflective surface 60 of annular ring 30 along a line 138 that is parallel to the X axis. The line beam 140 is reflected by reflective surface 60 at an angle that depends on the tilt of reflective surface 60 relative to laser diode 70. The photosensor array 74 is a linear photosensor array that is oriented perpendicular to line beam 140. As is apparent in FIG. 3, line beam 140 is incident on photosensor array 74 at a location that is a function of a tilt angle 144 of reflective surface 60 relative to laser diode 70. Thus, a photosensor element 146 of array 74 that intercepts beam 140 is representative tilt angle 144.

Photosensor array 72 may be a linear photosensor array and is aligned parallel to the line beam 140. Photosensor array 72 is positioned to intercept line beam 140 when the tilt angle of reflective surface 60 relative to treatment head 12 is zero. The laser diode 70 is positioned relative to annular ring 30 such that a portion of line beam 140 is intercepted by reflective surface 60 and a portion of line beam 140 passes an edge 142 of reflective surface 60 and is therefore not reflected. Thus, the length of line beam 140 that is reflected to and illuminates photosensor array 72 depends on the position of annular ring 30 relative to laser diode 70 in the X direction. That is, as treatment head 12 moves along the X direction relative to annular ring 30, more or less of photosensor array 72 is illuminated by reflected line beam 140. Thus, the illuminated portion of photosensor array 72 is representative of the X position of treatment head 12 relative to annular ring 30.

Sensing assembly 52 may have the same configuration as sensing assembly 50, but is oriented for sensing Y position and X axis tilt. In sensing assembly 52, the line beam generated by laser diode 80 is incident on reflective surface 60 along a line that is parallel to the Y axis for sensing of Y position and X axis tilt as described above.

Figure 4:
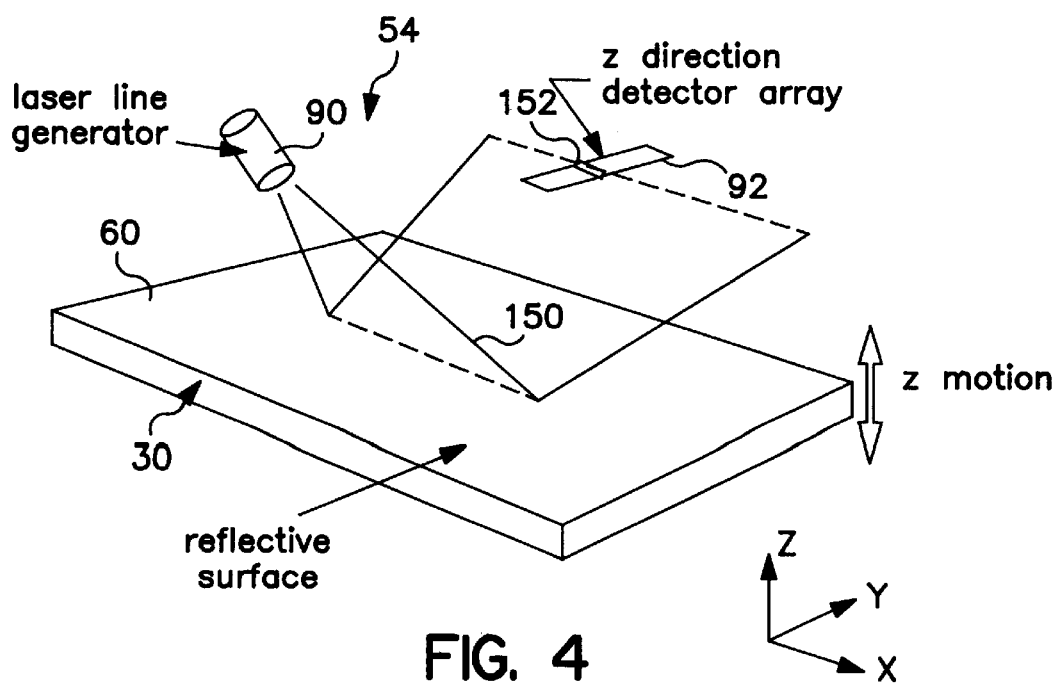
FIG. 4 is a schematic diagram of a second type of laser sensing assembly used in the soft docking system of FIGS. 1 and 2.

A pictorial diagram of sensing assembly 54 is shown in FIG. 4. Laser diode 90 directs a fan line beam 150 at reflective surface 60 on annular ring 30. It is assumed that annular ring 30 has been aligned so that reflective surface 60 is perpendicular to electron beam 14. Photosensor array 92 is a linear photosensor array that is oriented perpendicular to line beam 150. The line beam 150 is incident on reflective surface 60 at a relatively shallow angle of incidence and is reflected to photosensor array 92. The reflected line beam 150 is incident on photosensor array 92 at a position that is a function of the position of reflective surface 60 along the Z axis relative to treatment head 12. Thus, an element 152 of photosensor array 92 that is illuminated by reflected line beam 150 is representative of the Z position of treatment head 12 relative to applicator 20.

Figure 5:
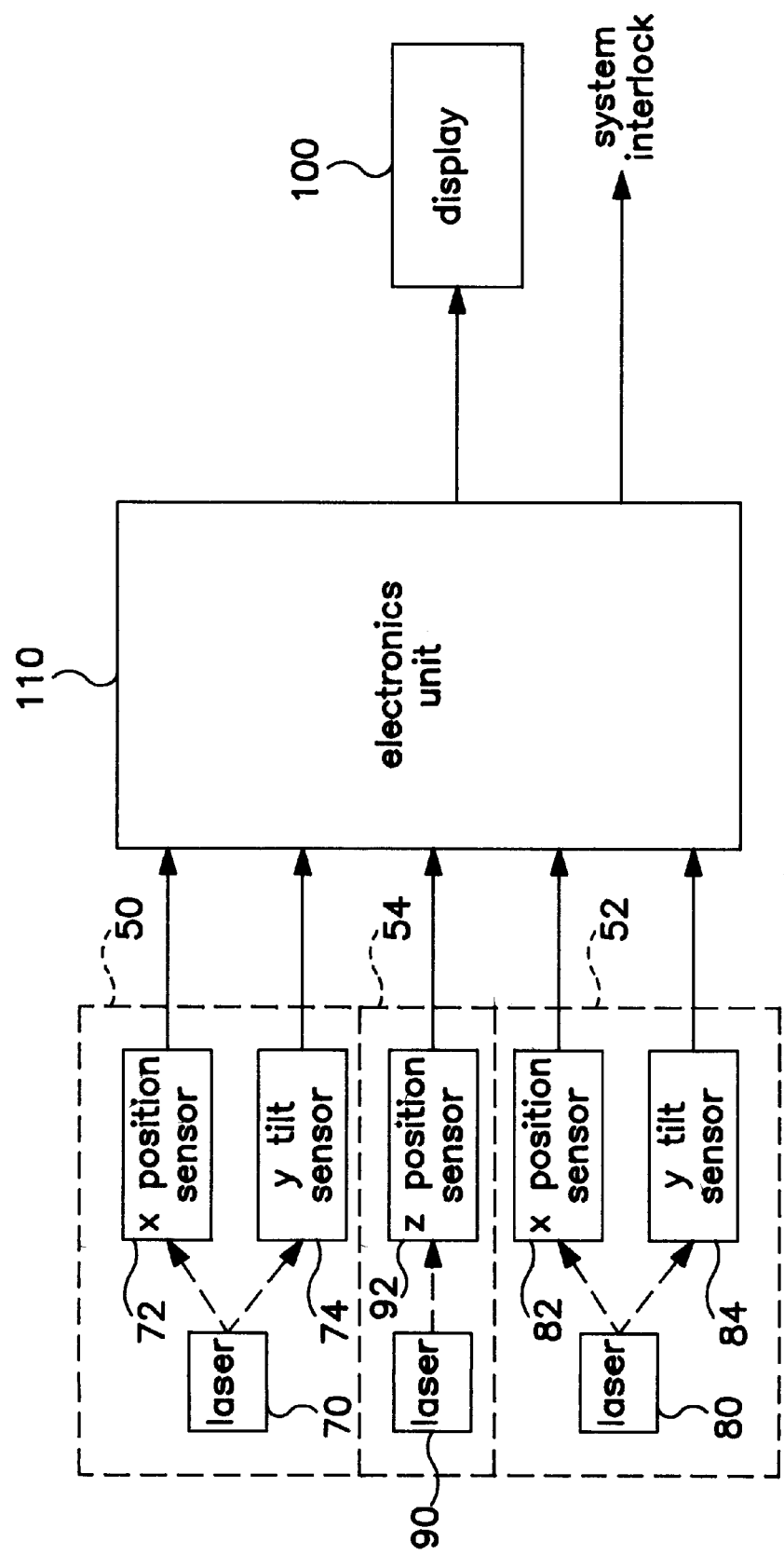
FIG. 5 is a block diagram of the soft docking system of the invention.

Since ambient light may interfere with operation of the system, a narrow bandpass optical filter is preferably positioned in front of each of the photosensor arrays 72, 74, 82, 84 and 92. Each bandpass optical filter has a passband that corresponds to the wavelength of the respective laser diode. As shown in FIG. 5, the output signals from photosensors 72, 74, 82, 84 and 92 are supplied to electronics unit 110. The electronics unit 110 includes conventional circuitry which converts the output signals of the respective photosensors to signals for driving display 100. In particular, the electronics unit 110 energizes one or more LED's in each of the LED arrays 120, 122, 124, 126 and 128 in display 100.

The number of illuminated elements in LED array 122 is determined from the number of elements of photosensor array 72 which intercept line beam 140 (FIG. 3). Thus, as the treatment head 12 is moved in the X direction relative to applicator 20, the number of elements of LED array 122 changes. Similarly the number of illuminated elements of LED array 120 indicates the Y position of treatment head 12 relative to applicator 20, as determined from photosensor array 82.

An element of LED array 126 is illuminated depending on the element 146 of photosensor array 74 (FIG. 3) which intercepts line beam 140. As the Y axis tilt angle 144 of applicator 20 relative to treatment head 12 is changed, different elements of LED array 126 are illuminated. When the Y axis tilt angle 144 of treatment head 12 relative to applicator 20 is zero, element 162 of LED array 126 is illuminated. Similarly, element 164 of LED array 124 is illuminated when the X axis tilt angle of treatment head 12 relative to applicator 20 is zero.

An element of LED array 128 is illuminated, depending on the element 152 of photosensor array 92 (FIG. 4) which intercepts line beam 150. When treatment id head 12 has the correct Z position relative to applicator 20, element 166 of LED array 128 is illuminated. When the X, Y and Z positions, and the X axis and Y axis tilt are all correct, indicating that the treatment head 12 and applicator 20 are aligned in both position and tilt angle, central element 160 of LED arrays 120 and 122 is illuminated.

In each case, the illuminated element of the respective LED array in display 100 depends on the location of the respective line beam on the corresponding photosensor array. The elements of LED arrays 120, 122,124,126 and 128 may be color coded to highlight the correct alignment. For example, red LED's may be used to indicate incorrect alignment, and LED's 160,162, 164 AND 166, which indicate correct alignment, may be green.

The electronics unit 110 preferably further includes a system interlock feature. The electronics unit 110 provides a system interlock signal to the portion of the treatment system 10 associated with generating electron beam 14. The system interlock signal prevents generation of electron beam 14 until treatment head 12 is correctly positioned and oriented with respect to applicator 20. Thus, the electronics unit 110 may include a circuit for monitoring the X, Y and Z positions and the X and Y tilt angles of treatment head 12 relative to applicator 20. When the correct X, Y and Z positions and the correct X and Y tilt angles are achieved, as indicated by the illumination of elements 160, 162, 164 and 166 in display 100, the system interlock signal enables generation of electron beam 14.

In operation, the display 100 is used by an operator to align treatment head 12 relative to applicator 20. In particular, the operator may use a position controller 200 shown in FIG. 1 to control the position and orientation of treatment head 12 relative to applicator 20. The position controller 200 may control motors which adjust the position and orientation of treatment head 12. The position controller 200 may, for example, have control buttons for changing the X, Y and Z positions and the X and Y tilt angle of treatment head 12 relative to applicator 20. The operator manipulates the position controller 200 until display 100 indicates that treatment head 12 is properly positioned relative to applicator 20. At this time, the system interlock signal enables generation of electron beam 14, and the prescribed treatment may be applied to the patient.

An example of an alignment operation utilizing the soft docking system of the invention is now given. As the treatment head 12 is tilted in one plane, one LED in the curved array corresponding to that plane is illuminated. The illuminated LED indicates the tilt of the treatment head in that plane. When the electron beam axis is perpendicular to the reflecting surface in that plane, only the middle LED is illuminated in the corresponding LED array. The tilt LED for the orthogonal plane operates in a similar fashion. When the electron beam axis is perpendicular to the reflective surface 60 in two orthogonal planes, the treatment head 12 is moved to center the applicator 20 with respect to the beam axis in the X and Y directions. As the treatment head is moved, for example, in the X direction, part of the horizontal LED array 122 is illuminated. When the treatment head is centered on the electron beam axis in the X direction, half of the LED's in the LED array 122 will be illuminated, including the two LEDs on either side of the large center element 160. Treatment head motion in the Y direction illuminates the vertical LED array 120 in a similar fashion. As the distance of the treatment head 12 from applicator 20 in the Z direction is varied, single elements corresponding to the Z distance are illuminated in the LED array 128. When the Z position is correct, the center element 166 of LED array 128 is illuminated. If the treatment head 12 is aligned relative to applicator 20 with respect to both position and tilt angle, the large center element 160 on the display will illuminate, indicating that docking is complete and that the interlock signal has been activated.

To overcome problems associated with interference from ambient light, the laser beams in the soft docking systems may be modulated. Synchronous detection by AC coupled photodetectors may eliminate the need for optical bandpass filters. When two dimensional photodetectors and LED displays are used, the system may be implemented with only two lasers and two detectors. The LED display then has only one LED array for sensing X and Y positions and one LED array for sensing Z position.

While there have been shown and described what are at present considered the preferred embodiments of the present invention, it will be obvious to those skilled in the art that various changes and modifications may be made therein without departing from the scope of the invention as defined by the appended claims.

What is claimed is:

1. In a medical treatment system that comprises a treatment head, an applicator independent of and separate from said head and having a fixed position relative to a patient and means for adjusting the position of the treatment head relative to the applicator, a soft docking system comprising:

one or more sensing assemblies for sensing a position of the treatment head relative to the applicator and providing one or more position signals representative thereof; and a display responsive to said position signals for indicating the position of the treatment head relative to the applicator, wherein the position of the treatment head may be adjusted so that said display indicates a desired position.

2. A soft docking system as defined in claim 1 wherein said sensing assemblies include sensing assemblies for sensing X position, Y position, Z position, X axis tilt and Y axis tilt of the treatment head relative to the applicator.

3. A soft docking system as defined in claim 1 wherein said sensing assemblies include a first sensing assembly for sensing X position and Y axis tilt, a second sensing assembly for sensing Y position and X axis tilt and a third sensing assembly for sensing Z position.

4. A soft docking system as defined in claim 3 wherein said first and second sensing assemblies each comprise a laser line generator coupled to the treatment head for directing a line beam at a reflective surface rigidly coupled to the applicator so that a portion of the line beam is reflected by the reflective surface, a position photosensor array coupled to the treatment head for intercepting the portion of said line beam that is reflected by said reflective surface and providing a position signal, wherein the portion of said line beam reflected by said reflective surface varies with the position of said applicator and is indicative of the position of said applicator, and a tilt photosensor array coupled to the treatment head and oriented perpendicular to said line beam for sensing the tilt of said reflective surface relative to the treatment head and providing a tilt signal.

5. A soft docking system as defined in claim 3 wherein said third sensing assembly comprises a laser line generator coupled to the treatment head for directing a line beam at a reflective surface rigidly coupled to said applicator and a Z direction photosensor array coupled to the treatment head and oriented perpendicular to said line beam for sensing said line beam and providing a Z position signal.

6. A soft docking system as defined in claim 1 wherein said display is mounted on the treatment head.

7. A soft docking system as defined in claim 1 wherein said display comprises first, second, third, fourth and fifth LED arrays representative of X position, Y position, Z position, X axis tilt and Y axis tilt, respectively, wherein an illuminated LED in each of said first, second and third LED arrays is representative of the position of the treatment head relative to the applicator and an illuminated LED in each of the fourth and fifth LED arrays is representative of tilt angle of the treatment head relative to the applicator.

8. A soft docking system as defined in claim 1 further comprising means responsive to said position signals for generating an interlock signal that inhibits the treatment head from applying treatment to the patient except when said position signals indicate a desired position of the treatment head relative to the applicator.

9. A medical treatment system comprising:

a treatment head for applying a medical treatment to a patient;

an applicator independent of said treatment head having a fixed position relative to the patient;

one or more sensing assemblies for sensing a position of the treatment head relative to the applicator and providing one or more position signals representative thereof;

a display responsive to said position signals for indicating the position of said treatment head relative to said applicator; and means for adjusting the position of the treatment head relative to the applicator in response to the indicated position.

10. A medical treatment system as defined in claim 9 wherein said applicator includes a reflective surface and wherein each of said one or more sensing assemblies is affixed to said treatment head and comprises a laser for directing a light beam at said reflective surface and a photodetector for sensing a reflected light beam.

11. A medical treatment system as defined in claim 10 wherein said treatment head includes means for directing an electron beam through said applicator to the patient, wherein said applicator comprises an applicator tube for passing said electron beam to the patient and wherein said reflective surface comprises an annular mirror surrounding said applicator tube.

12. A medical treatment system as defined in claim 9 wherein said sensing assemblies include sensing assemblies for sensing X position, Y position, Z position, X axis tilt and Y axis tilt of the treatment head relative to the applicator.

13. A medical treatment system as defined in claim 9 wherein said sensing assemblies include a first sensing assembly for sensing X position and Y axis tilt, a second sensing assembly for sensing Y position and X axis tilt and a third sensing assembly for sensing Z position.

14. A medical treatment system as defined in claim 13 wherein said first and second sensing assemblies each comprise a laser line generator coupled to the treatment head for directing a line beam at a reflective surface rigidly coupled to the applicator so that a portion of the line beam is reflected by the reflective surface, a position photosensor array coupled to the treatment head for intercepting the portion of said line beam that is reflected by said reflective surface and providing a position signal, wherein the portion of said line beam reflected by said reflective surface varies with the position of said applicator and is indicative of the position of said applicator, and a tilt photosensor array coupled to the treatment head and oriented perpendicular to said line beam for sensing the tilt of said reflective surface relative to the treatment head and providing a tilt signal.

15. A medical treatment system as defined in claim 13 wherein said third sensing assembly comprises a laser line generator coupled to the treatment head for directing a line beam at a reflective surface rigidly coupled to said applicator and a Z direction photosensor array coupled to the treatment head and oriented perpendicular to said line beam for sensing said line beam and providing a Z position signal.

16. A medical treatment system as defined in claim 9 wherein said display is mounted on the treatment head.

17. A medical treatment system as defined in claim 9 wherein said display comprises first, second, third, fourth and fifth LED arrays representative of X position, Y position, Z position, X axis tilt and Y axis tilt, respectively, wherein an illuminated LED in each of said first, second and third LED arrays is representative of the position of the treatment head relative to the applicator and an illuminated LED in each of the fourth and fifth LED arrays is representative of tilt angle of the treatment head relative to the applicator.

18. A medical treatment system as defined in claim 9 further comprising means responsive to said position signals for generating an interlock signal that inhibits the treatment head from applying treatment to the patient except when said position signals indicate a desired position of the treatment head relative to the applicator.

19. In a medical treatment system, a method for soft docking of a treatment head to an applicator having a fixed position relative to a patient, comprising the steps of:

positioning an applicator in a fixed position in respect to a treatment zone in a patient during a surgical procedure, sensing a position of the treatment head relative to the applicator and providing one or more position signals representative thereof, said applicator and said treatment head being independent elements in the system;

indicating the position of the treatment head relative to the applicator on a display in response to the position signals; and adjusting the position of the treatment head relative to the applicator so that the display indicates a desired position.

20. A medical treatment system in accordance with claim 19 including rigidly positioning the applicator relative to the patient by afixing the applicator to a support table for the patient and aligning the treatment head collinearly with the axis of the applicator by controlling the X, Y and Z position of the treatment head relative to the applicator and by controlling the tilt and rotational angle of the treatment head along the X and Y axes relative to the applicator.

* * * * *